US012606463B2

(12) United States Patent
Wu et al.

(10) Patent No.: US 12,606,463 B2
(45) Date of Patent: Apr. 21, 2026

(54) METHOD FOR REPAIRING STEM CELLS AND USE THEREOF

(71) Applicant: Siyuan Wu, Beijing (CN)

(72) Inventors: Siyuan Wu, Beijing (CN); Xinwei Wang, Beijing (CN); Linze Wu, Beijing (CN)

(73) Assignee: INTERNATIONAL DIGITAL GENETIC ENGINEERING AB, Helsingborg (SE)

( * ) Notice: Subject to any disclaimer, the term of this patent is extended or adjusted under 35 U.S.C. 154(b) by 1097 days.

(21) Appl. No.: 17/636,981

(22) PCT Filed: Aug. 23, 2020

(86) PCT No.: PCT/CN2020/110682
§ 371 (c)(1),
(2) Date: Feb. 21, 2022

(87) PCT Pub. No.: WO2021/036964
PCT Pub. Date: Mar. 4, 2021

(65) Prior Publication Data
US 2022/0289597 A1 Sep. 15, 2022

(30) Foreign Application Priority Data

Aug. 23, 2019 (CN) .......................... 201910786774.4

(51) Int. Cl.
*C02F 1/30* (2023.01)
*C12N 5/0775* (2010.01)
*C02F 103/04* (2006.01)

(52) U.S. Cl.
CPC .............. *C02F 1/30* (2013.01); *C12N 5/0665* (2013.01); *C02F 2103/04* (2013.01); *C12N 2500/00* (2013.01)

(58) Field of Classification Search
CPC .. C02F 1/30; C02F 1/487; C02F 1/005; C02F 1/34; C02F 2103/04; C02F 2103/026;
(Continued)

(56) References Cited

FOREIGN PATENT DOCUMENTS

CN 1280101 A * 1/2001 ................ C02F 1/30
CN 102228718 A * 11/2011 ........... C12N 5/0797
(Continued)

OTHER PUBLICATIONS

CN 1280101 A English description, Jan. 17, 2001, Wu Siyuan.*
(Continued)

*Primary Examiner* — Akash K Varma
(74) *Attorney, Agent, or Firm* — Veros Legal Solutions, LLP

(57) ABSTRACT

The present invention falls within the technical field of cell repair, and specifically relates to a method for repairing stem cells and a use thereof. On the basis of the original invention technology, following improvement, in the present invention, pulse wave-treated water having the function of repairing stem cells is obtained by means of pulse wave-treated water having pulse wave sequences with equal widths and unequal intervals, and the method has additive effects on multiple treated samples. Without influencing cell proliferation, a culture system prepared from the pulse wave-treated water can not only reduce the natural apoptosis effect of human umbilical cord mesenchymal stem cells (H-MSC), but also can inhibit injury-induced H-MSC apoptosis, and has a cell repair effect.

5 Claims, 5 Drawing Sheets

(58) Field of Classification Search
CPC .. C12N 5/0665; C12N 5/0668; C12N 5/0602;
C12N 5/0605; C12N 5/0606; C12N
5/0623; C12N 5/0775; C12N 5/071;
C12N 5/073; C12N 5/0735; C12N
5/0797; C12N 2500/00; C12N 2500/05;
C12N 2529/00; A23L 2/00; A23L 2/52;
A23L 33/00; A61L 27/38; G06T 5/00;
G06T 7/90
USPC ..................................................... 210/748.01
See application file for complete search history.

(56) References Cited

FOREIGN PATENT DOCUMENTS

| | | | | | |
|----|------------|----|---|--------|------------|
| CN | 107540044  | A  | * | 1/2018 | ............... C02F 1/30 |
| CN | 110482643  | A  |   | 11/2019 | |
| EP | 3272713    | A1 |   | 1/2018 | |
| JP | 2000-093973 | A |   | 4/2000 | |
| JP | 2001-286866 | A |   | 10/2001 | |
| WO | 2020-262540 |   |   | 12/2020 | |

OTHER PUBLICATIONS

CN 102228718 A English description, Nov. 2, 2011, Changyong
Wang et al.*
CN 107540044 A English description, Jan. 5, 2018, Zhu Fangfang
et al.*

* cited by examiner

METHOD FOR REPAIRING STEM CELLS AND USE THEREOF

FIELD OF THE INVENTION

The present invention relates to the technical field of cell repairing, and more particularly, to a method for repairing stem cells and use thereof.

BACKGROUND

Water is a vital energy source, and a water source in an original state was crystal clear and tasted sweet. However, with an accumulation of both time and material, the environment has become worse, the water source in the original state has lost an original appearance thereof, and a frequency of a water source having been destroyed has a huge variation occurred. Due to a plurality of high-rise buildings standing in a modern city, a plurality of interlaced magnetic waves has interfered with the frequency, and at a same time, a biological frequency of a human is disturbed and destroyed, resulting in a pathological change appearing in a living body, and an occurrence of a disease.

In the prior art, an existing pulse code technology is mostly applied in an electronics industry. On Jul. 12, 1999, the present applicant has applied for a Chinese patent of invention entitled "An Improved Pulse Treating Apparatus" (issued patent number: CN1119289C), the patent disclosed that by setting a pulse sequence and a pulse interval of a pulse instrument, and forming a specific pulse period, after a far-infrared radiation wave formed by the pulse period is applied to treating food, a concentration of a plurality of free radicals in the food will be reduced, achieving a health care effect. However, an application range of such a treatment technology is limited.

According to a plurality of deficiencies in the prior art and the patent technology disclosed by the applicant before, the applicant has improved a plurality of specific parameters and a treatment method for a pulse treatment technology in the prior art, before treating drinking water with the method having been improved and obtaining a pulse wave treated water, while the method has an additive effect on a plurality of treated samples. When culturing a plurality of stem cells in a medium prepared with the pulse wave-treated water, without affecting a normal proliferation of the stem cells, a natural apoptosis and a damage-induced apoptosis of the stem cells can be inhibited, having an effect of repairing the stem cells.

BRIEF SUMMARY OF THE DISCLOSURE

Aiming at the technical problem stated above, the purpose of the present invention is providing a method for a pulse wave treating water, the method includes: adopting a pulse wave with a power of 28 W and a frequency of 1.5M to radiate and treat drinking water, the pulse wave is composed of a plurality of repeated pulse sequences, the repeated pulse sequence is composed of a first pulse sequence and a second pulse sequence in an interval, both the first pulse sequence and the second pulse sequence are composed of four pulses and four intervals, a duty ratio of the four pulses of the first pulse sequence is equal, a range of the duty ratio of the pulse is 1.3-3.5 μs, the intervals between the four pulses are equal, and a range of the interval between the pulses is 0.7-3.1 μs; a duty ratio of the four pulses of the second pulse sequence is equal, and a range of the duty ratio of the pulse is 1.1-3.9 μs, a first pulse and a third pulse have an interval between the pluses equal, a range of the interval between the pulses is 1.8-4.6 μs, a second pulse and a fourth pulse have an interval between the pluses equal, a range of the interval between the pulses is 0.9-2.3 μs.

Preferably, a number of times of the pulse wave radiating and treating the drinking water is two, 30 minutes for each.

An object of the present invention is providing another method for the pulse wave treating water, the method includes: adopting a pulse wave having a power of 35 W and a frequency of 1.9M, to radiate and treat drinking water, the pulse wave is composed of a plurality of repeated pulse sequences, the repeated pulse sequence is composed of a first pulse sequence and a second pulse sequence in an interval, both the first pulse sequence and the second pulse sequence are composed of four pulses and four intervals, a duty ratio of the four pulses of the first pulse sequence is equal, a range of the duty ratio of the pulse is 1.3-3.5 μs, the intervals between the four pulses are equal, and a range of the interval between the pulses is 0.7-3.1 μs; a duty ratio of the four pulses of the second pulse sequence is equal, and a range of the duty ratio of the pulse is 1.1-3.9 μs, a first pulse and a third pulse have an interval between the pluses equal, a range of the interval between the pulses is 1.8-4.6 μs, a second pulse and a fourth pulse have an interval between the pluses equal, a range of the interval between the pulses is 0.9-2.3 μs.

Preferably, a number of times of the pulse wave radiating and treating the drinking water is one, 30 minutes in total.

Preferably, the pulse wave is generated by a pulse treating apparatus, the pulse treating apparatus comprises a pulse sequence generator 1, a driving circuit 2, a radiator 7, a treating platform 11 and a space storage area; the treating platform 11 has drinking water or ultrapure water arranged; the pulse sequence generator 1 is composed of a high-frequency oscillator A, a pulse storage frequency dividing circuit B and a frequency mixing circuit C, the high-frequency oscillator A, the pulse storage frequency dividing circuit B and the frequency mixing circuit C are connected in series; the pulse sequence generator 1 connects with the radiator 7 through the driving circuit 2; the space storage area locates below the radiator 7, and the treating platform 11 locates on the space storage area; a high-frequency oscillation wave generated by the high-frequency oscillator A is modulated and coded by the pulse storage frequency division circuit B and the frequency mixing circuit C before forming a pulse sequence, the pulse sequence formed is amplified by the driving circuit 2 before being added to the radiator 7; and the pulse wave radiated by the radiator 7 radiates to the drinking water or the ultrapure water placed on the treating platform 11.

Preferably, a position of the space storage area may be freely adjusted, to ensure that an incident pulse wave forms a plurality of different radiation heights and radiation angles with the water, and a range of the radiation angle is 0-90°.

Preferably, the radiation angle is 45°, and the radiation height is 55 cm.

Another object of the present invention is providing a pulse wave treated water obtained after being treated by the pulse wave, the pulse wave treated water is a pulse wave treated drinking water or a pulse wave treated ultrapure water.

Another object of the present invention is providing a method for repairing a stem cell in vitro, comprising a plurality of following steps:

(1) resuscitating, regenerating and proliferation the stem cells;

(2) using the pulse wave treated ultrapure water to dissolve Gibco/DMEM dry powder culture medium, before reaching a constant volume of 1 L, to prepare and obtain an induction culture medium;

(3) after culturing the stem cells for 24 hours, replacing to an induction culture medium for an induction culture.

Preferably, the stem cells comprise embryonic stem cells, umbilical cord stem cells, placenta stem cells, neural stem cells, muscle stem cells, or umbilical cord blood stem cells.

Preferably, the stem cells are human umbilical cord mesenchymal stem cells.

Another object of the present invention is providing an application of the pulse wave treated ultrapure water in preparing a culture system for promoting the repair of the stem cells in vitro.

Preferably, the stem cells comprise normal stem cells, natural apoptotic stem cells, DMSO-induced damaged stem cells, positive drug A+B induced damaged stem cells, scratched stem cells.

Another object of the invention is providing an application of the pulse wave treated drinking water in preparing traditional Chinese medicine products, health products, foods, drinking or cosmetics.

Benefits of the present invention: (1) by defining a waveform, a frequency and a power of the pulse wave, radiating and treating the drinking water with the pulse wave, to obtain the pulse wave treated water; by the method for treating water with the pulse wave, it is possible to change an angle of a hydrogen-oxygen bond in a water molecular structure without contacting the water, increasing a dissolved oxygen content in the water, improving a content of a plurality of beneficial elements in the water including strontium, potassium, calcium and iron, while decreasing a plurality of heavy metal elements including arsenic, barium, separation, manganese and more, as well as a plurality of organic matters; (2) the method has an additive effect on a plurality of treated samples; (3) the pulse wave treated water obtained by the present invention is able to inhibit the apoptosis of the stem cells, have a repair action on the stem cells, especially for repairing the human umbilical cord mesenchymal stem cells; (4) the pulse wave treated water obtained by the present invention has basically no effect on proliferation of the stem cell, being safe and reliable for growth and development of the stem cell.

BRIEF DESCRIPTION OF THE DRAWINGS

FIG. 2a illustrates a growth-proliferation curve on the H-MSC cells; FIG. 2b illustrates a proliferation on the H-MSC cells after culturing;

FIG. 4a illustrates a cell mortality variation curve of the H-MSC cells; FIG. 4b illustrates a cell mortality number after a 24 hours inoculation of the H-MSC cells;

FIG. 6 illustrates a plot on a DMSO-induced injury and death of the H-MSC cells; wherein FIG. 6A illustrates an induced injury variation curve of the H-MSC cells; FIG. 6B illustrates an induced death number after inoculating the H-MSC cells for 24 hours;

FIG. 8 illustrates a plot on a positive reagent-induced injury and death of the H-MSC cells; wherein FIG. 8a illustrates an induced injury variation curve of the H-MSC cells; FIG. 8b illustrates an induced death number after inoculating the H-MSC cells for 24 hours.

DETAILED DESCRIPTION OF EMBODIMENTS

Figure 1:
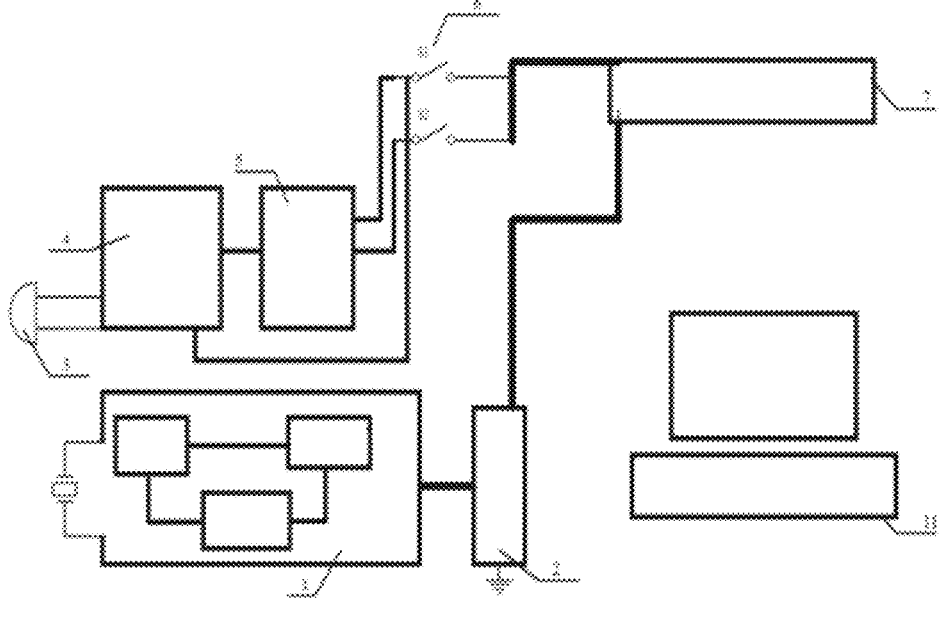
FIG. 1 illustrates a circuit diagram on a pulse treating apparatus, wherein: 1—pulse sequence generator, 2—driving circuit, 3—alarm circuit, 4—main CPU control unit, 5—power converter, 6—gear shift switch, 7—radiator, 8—space storage area I, 9—space storage area II, 10—water, 11—treating platform, A—high frequency oscillator, B—pulse storage frequency division circuit, C—frequency mixing circuit.

Further detailed descriptions of the present invention are stated hereafter, referencing to the embodiments of the present invention. It should be understood that the present invention is not limited to the embodiments listed hereafter. Those skilled in the art can improve or transform the applications according to the descriptions, all of these improvements and transforms should belong to the scope of protection in the appended claims of the present invention. Description of Related Terms and Instrument Materials in Embodiments:

All pulse wave treated water in the embodiments of the present invention is life water obtained by using pulse wave to treat ultrapure water.

The life water in the present invention refers to a pulse wave treated water obtained by treating drinking water through a pulse wave radiation, which has a radiation angle smaller than 90 degrees, a water quality of the pulse wave treated water obtained by a pulse wave having a radiation angle 45 degrees is an optimal.

Main instrument: a real-time dynamic living cell imaging system (RT-LCI); a $CO_2$ incubator, a coding pulse treating apparatus (obtained by improving a pulse treating apparatus stated in a patent with a patent number ZL99109583.9);

Main material: human umbilical cord mesenchymal stem cell P4 generation (H-MSC) (Saliai SC-08-003, NA); cell culture 6-well plate (Coming 3516, 1966040728); Essen #4379-ImageLock Plates culture plate (Essen 4379, 17050401); Death Dye Cell Killing-488 (Themro YOYO-1, NA); DMSO (Sigma RNBG989, 202008); Apoptosis-Positive Induction Reagent (Apoptosis-Inducing Reagent A+Apoptosis-Inducing Reagent B) (Beyotime C0005, NA); life water-1, which is the pulse wave treated water obtained by adopting a pulse wave with a power of 28 W and a frequency of 1.5M, to treat ultrapure water twice for 30 minutes each; life water-2, which is the pulse wave treated water obtained by adopting a pulse wave with a power of 35 W and a frequency of 1.9M, to treat ultrapure water once for 30 minutes in total.

Embodiment 1, a Pulse Treating Apparatus and a Working Principle Thereof

A pulse treating apparatus, comprises a pulse sequence generator 1, a driving circuit 2, an alarm circuit 3, a main CPU control unit 4, a power converter 5, a gear shift switch 6, a radiator 7, a treating platform 11 and a space storage area; the space storage area comprises a space storage area I and a space storage area II, the space storage area I and the space storage area II are arranged in parallel, to ensure that an incident angle of the pulse wave is less than 90 degrees, the treating platform 11 has ultrapure water arranged; the pulse sequence generator 1 is composed of a high-frequency oscillator A, a pulse storage frequency dividing circuit B and a frequency mixing circuit C, which are connected in series; the pulse sequence generator 1 connects with the radiator 7 through the driving circuit 2; the space storage area locates below the radiator 7, and the treating platform 11 locates on the space storage area; the main CPU control unit 4 connects respectively with the alarm circuit 3, the power converter 5 and the gear shift switch 6, the gear shift switch 6 further connects with the power converter 5 and the radiator 7 respectively, the gear shift switch 6 comprises a first gear S1 and a second gear S2, a power of the first gear is 28 W, with a frequency of 1.5M; and a power of the second gear is 35 W, with a frequency of 1.9M;

A working principle of the pulse treating apparatus: first, the main CPU control unit 4 is responsible for controlling a plurality of keys, indication lamps, alarms and timers on a panel, and sending an instruction to the alarm circuit 3, the power converter 5 and the gear shift switch 6. The power converter 5 outputs a treated voltage to a plurality of different units, after the main supply (220V) is treated by a step-down transformer, so as to supply power to the whole system. Second, a high-frequency oscillation wave generated by the high-frequency oscillator A in the pulse sequence generator 1 is modulated and encoded by the pulse storage frequency division circuit B and the frequency mixing circuit C, before forming a pulse wave sequence, the pulse wave sequence formed by encoding is added to the radiator 7 after a power thereof is amplified by the driving circuit 2. A pulse wave radiated by the radiator 7 radiates into the ultrapure water placed on the treating platform 11, and finally switching the gear shift switch 6 to adjust the power and the frequency of the pulse treating apparatus, so as to control a pulse intensity and a period of the pulse wave.

Embodiment 2: Obtaining the Life Water After Being Treated by the Pulse Treating Apparatus 2.1 Preparation of the Life Water.

Preparation of the life water-1: radiating and treating the ultrapure water twice by adopting the pulse wave generated by the improved pulse treating apparatus, 30 minutes for each. The pulse wave is composed of a plurality of repeated pulse sequences, the repeated pulse sequence is composed of a first pulse sequence and a second pulse sequence in an interval, both the first pulse sequence and the second pulse sequence are composed of four pulses and four intervals. A duty ratio of the four pulses of the first pulse sequence is equal, a range of the duty ratio of the pulse is 1.3-3.5 µs, the intervals between the four pulses are equal, and a range of the interval between the pulses is 0.7-3.1 µs. A duty ratio of the four pulses of the second pulse sequence is equal, and a range of the duty ratio of the pulse is 1.1-3.9 µs, a first pulse and a third pulse have an interval between the pluses equal, a range of the interval between the pulses is 1.8-4.6 µs, a second pulse and a fourth pulse have an interval between the pluses equal, a range of the interval between the pulses is 0.9-2.3 µs. A power of the pulse wave is 28 W, a frequency of the pulse wave is 1.5M, a radiation height is 55 cm, and a radiation angle is 45 degrees.

Preparation of the life water-2: radiating and treating the ultrapure water once by adopting the pulse wave generated by the improved pulse treating apparatus, for 30 minutes in total. The pulse wave is composed of a plurality of repeated pulse sequences, the repeated pulse sequence is composed of a first pulse sequence and a second pulse sequence in an interval, both the first pulse sequence and the second pulse sequence are composed of four pulses and four intervals. A duty ratio of the four pulses of the first pulse sequence is equal, a range of the duty ratio of the pulse is 1.3-3.5 µs, the intervals between the four pulses are equal, and a range of the interval between the pulses is 0.7-3.1 µs. A duty ratio of the four pulses of the second pulse sequence is equal, and a range of the duty ratio of the pulse is 1.1-3.9 µs, a first pulse and a third pulse have an interval between the pluses equal, a range of the interval between the pulses is 1.8-4.6 µs, a second pulse and a fourth pulse have an interval between the pluses equal, a range of the interval between the pulses is 0.9-2.3 µs. A power of the pulse wave is 35 W, a frequency of the pulse wave is 1.9M, a radiation height is 55 cm, and a radiation angle is 45 degrees.

2.2 Water Quality Detection Result.

The life water obtained after being treated by the pulse wave is detected by Laser Raman spectroscopy at Lanzhou University, and an angle of a hydrogen-oxygen bond structure of a water molecule is expanded to 180 degrees from 104.5 degrees, being non-polar. Angles of electron clouds of both hydrogen and oxygen atoms in water are overlapped, a dissolved oxygen content in the water is increased by more than 12%, and a pH value is weakly alkaline; and a detection by a specific department of the national medical products administration shows that a plurality of beneficial elements, including strontium, potassium, calcium, iron and more, are increased, and a plurality of heavy metal elements including arsenic, barium, septum, manganese and more, are decreased, and a plurality of organic matters are reduced; and a plurality of water scales in a kettle is able to fall off automatically after boiling the life water.

The method has a superposition effect on a plurality of samples for treating.

Embodiment 3: H-MSC Cells Growth & Proliferation Experiment 3.1 Grouping and Culturing.

H-MSC cells, after resuscitation, proliferation and expansion, are observed under a microscope to ensure a good state of the cells, and when a fusion degree of the cells reaches 80%, the cells are divided into four groups (a normal group, a control group, a life water-1 group and a life water-2 group), before being inoculated respectively onto a 6-well plate, each well has an inoculation amount of $1.2*10^5$, and a culture system of 2 ml.

3.2 Culturing.

After the cells are inoculated for 24 hours, a culture medium is replaced for an induction culture, and a culture condition is: an H-DMEM culture medium +10% FBS (BI fetal bovine serum) +1% double antibody +5% $CO_2$ +37° C. The H-DMEM culture medium of the normal group is a commercial H-DMEM culture medium (Coming 03318002, 201908); the culture medium of the control group is prepared by the ultrapure water dissolving Gibco/DMEM dry powder culture medium; the culture medium of the life water-1 group is prepared by the life water-1 dissolving the Gibco/DMEM dry powder culture medium; and the culture medium of the life water-2 group is prepared by the life water-2 dissolving the Gibco/DMEM dry powder culture medium.

3.3 H-MSC Cells Growth and Proliferation Measurement.

Monitoring the Cells by a real-time dynamic imaging system, inducting and culturing the cells for 2 generations, observing and measuring a growth and proliferation condition of the H-MSC cells in 72 hours during the life water introduction and proliferation.

3.4 Measurement Results

Figure 2:
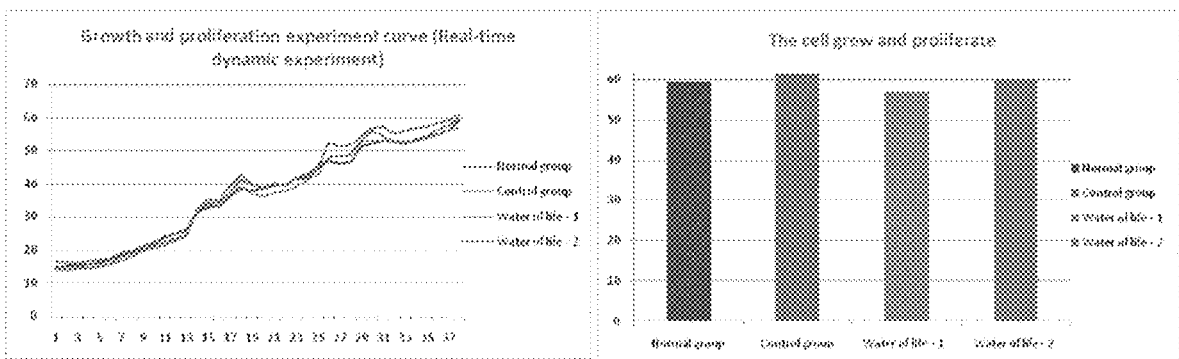
FIG. 2 illustrates a growth-proliferation chart on H-MSC cells.

Shown as FIG. 2, a growth curve of the H-MSC cells cultured in the culture medium prepared with the life water is basically consistent with that of the normal group and that in the culture medium prepared with the pure water, and after a 72 h-culture, a proliferation quantity of the H-MSC cells of both the life water-1 group and the life water-2 group has no significant difference from that of the control group and the normal group (wherein P>0.05, N=8). The result has shown that the life water will not affect a normal proliferation of the H-MSC cells, being safe and reliable for growth and development of the cells.

Embodiment 4: H-MSC Cells Natural Apoptosis Experiment 4.1 Grouping and Culturing.

Dividing the H-MSC cells into three groups (a control group, a life water-1 group and a life water-2 group), and after inducting and culturing the cells for 2 generations respectively, (an inducting and culturing mode is as same as that in section 2.2 of the embodiment 2,), when a fusion degree of the cells reached 60%, the cells are inoculated onto an Essen #4379ImageLock Plates culturing plate, each well has an inoculation amount of 8000, and a culture system of 150 μL.

4.2 H-MSC Cells Mortality Number Measuring.

Each group has three cells arranged as a parallel control, and after inoculating the cells for 24 hours, a death dye Ki488 with a final concentration of 1 μM is added, while monitoring the cells by a real-time dynamic imaging system, observing and measuring a variation condition of the cell mortality number.

4.3. Measuring Results

Figure 3:
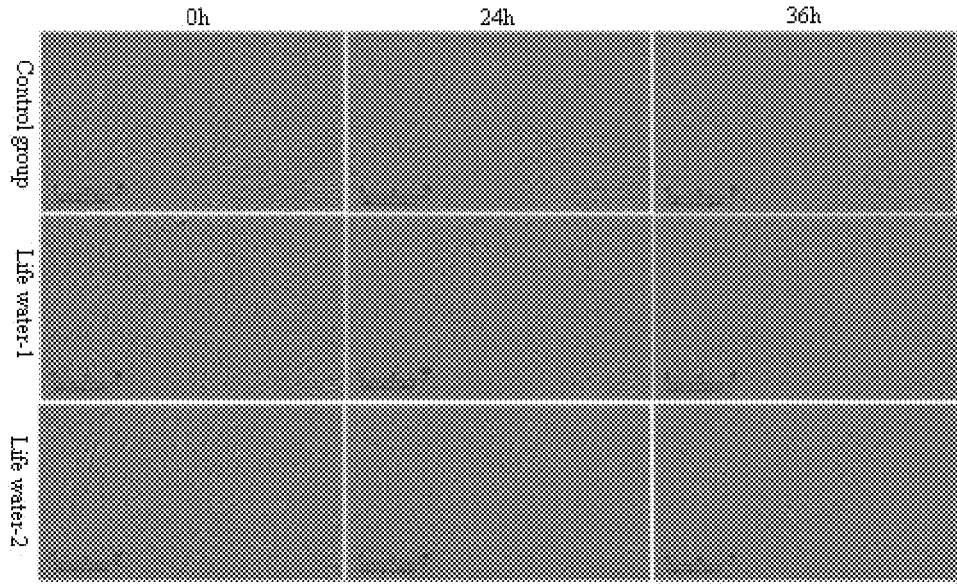
FIG. 3 illustrates a monitoring diagram on a changing condition of a cell mortality number of the H-MSC cells in a real-time dynamic imaging system.
Figure 4:
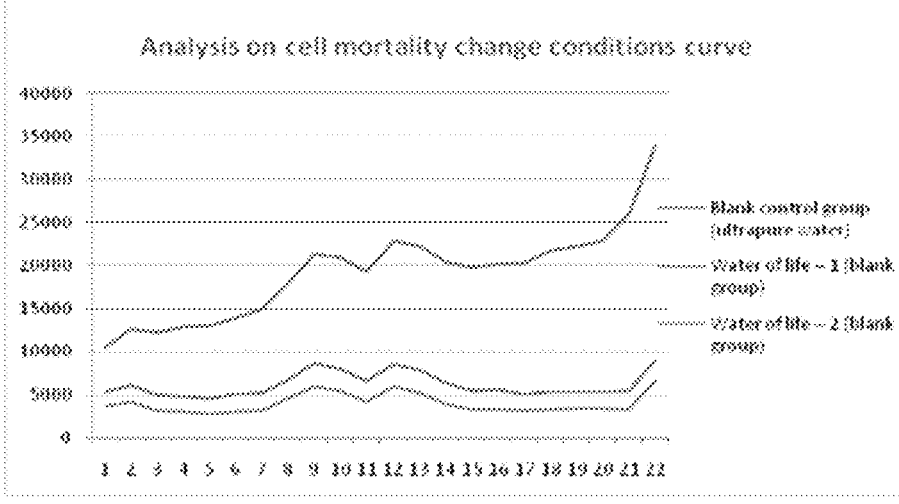
FIG. 4 illustrates a natural apoptosis graph of the H-MSC cells.
Figure 4:
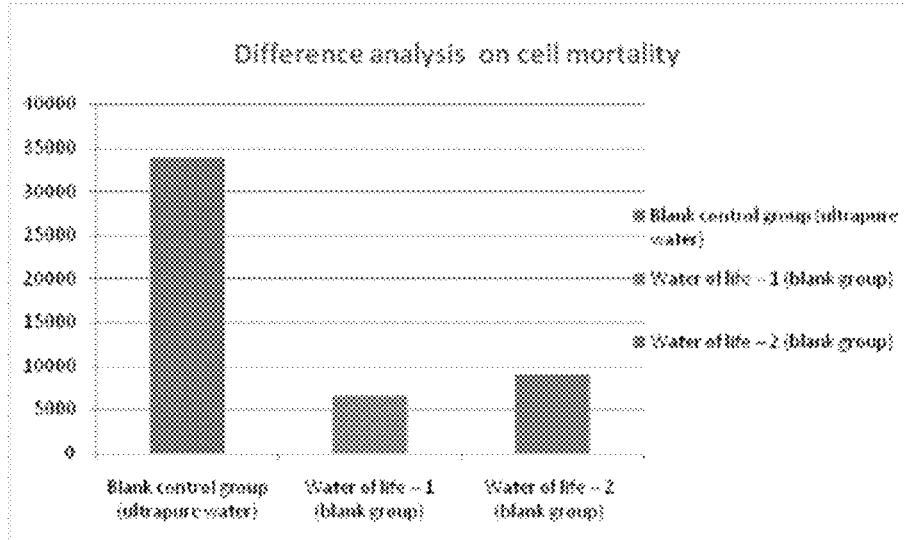

A monitoring result of the cells by the real-time dynamic imaging system is shown as FIG. 3, an H-MSC cells death of the control group is obvious, and compared with the control group, an H-MSC cells death in the life water-1 group and the life water-2 group is obviously reduced. A result of FIG. 4 shows that cell mortality curves of H-MSC cells in the life water-1 group and the life water-2 group are slower and lower than that of the control group; the cell death number, after 24 hours culturing, are significantly lower than that of the control group (P<0.001, N=8), which has stated that, the culturing system with the life water having been treated by different pulse intensions, for the natural apoptosis of the H-MSC cells, has shown an activity to the cells, being able to inhibit the natural apoptosis of the cells, having a significant difference when comparing the number of death to that of the control group, which has proven that the life water is able to promote metabolism, change a cell environment, and guarantee a normal differentiation of the cells.

Embodiment 5: H-MSC Cells-Induced Killing Experiment 5.1, 2% DMSO-Induced H-MSC Cells Injury Experiment
5.1.1 Grouping and Culturing
Grouping and culturing are same as the step 3.1 of embodiment 3

5.1.2 H-MSC Cells Mortality Number Measuring.

Each group has three cells arranged as a parallel control, and after inoculating the cells for 24 hours, each group of cells is changed to a culture medium containing 2% DMSO, then a death dye Ki488 with a final concentration of 1 μM is added, while monitoring the cells by a real-time dynamic imaging system, observing a variation condition of the natural injury and death number of the H-MSC cells induced by 2% DMSO.

5.1.3 Measurement Results

Figure 5:
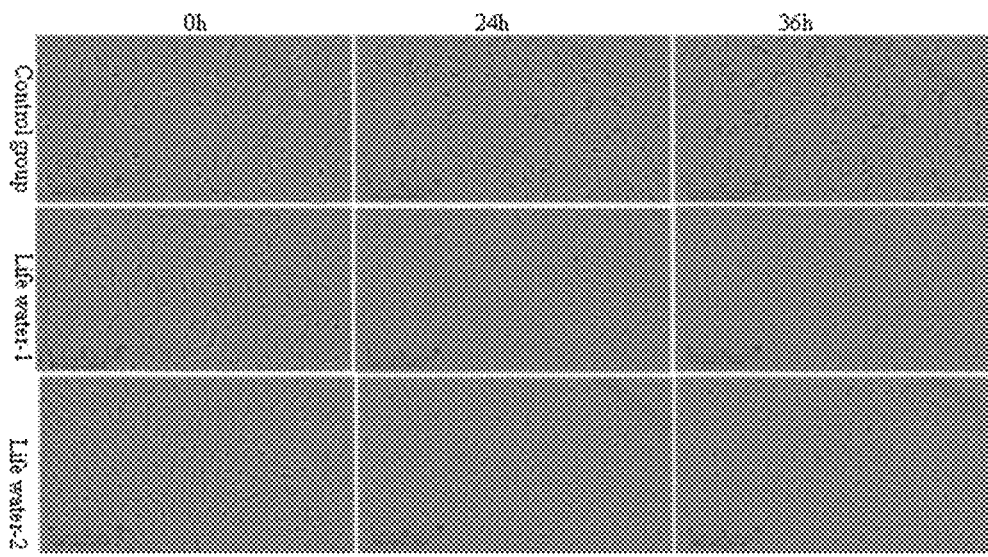
FIG. 5 illustrates a monitoring graph on a variation condition of a DMSO-induced injury and death number of the H-MSC cells by a real-time dynamic imaging system.
Figure 6:
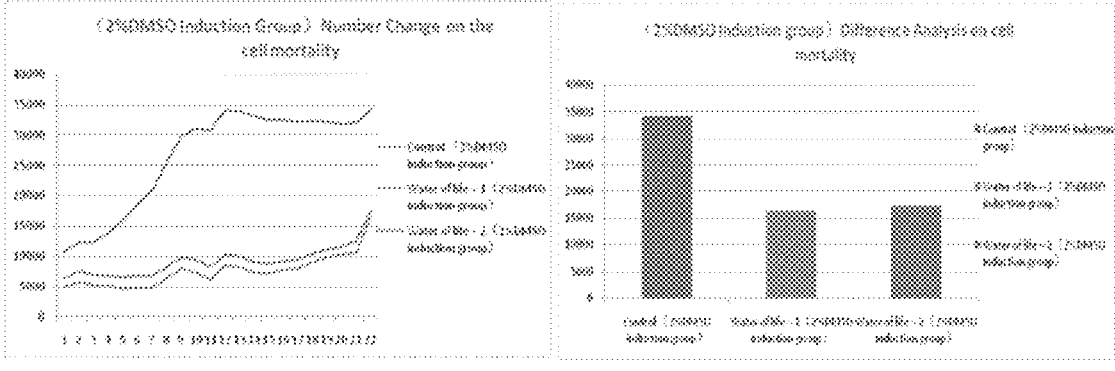

A monitoring result of the cells by the real-time dynamic imaging system is shown as FIG. 5, the H-MSC cells in the control group has a significant death after being induced by the 2% DMSO, compared with the control group, the H-MSC cells death in the life water-1 group and the life water-2 group are obviously reduced. A result of FIG. 6 shows that, a death curve of the H-MSC cells in the life water-1 group and the life water-2 group after being induced by the 2% DMSO is slow and lower than that of the control group; the cell death number, after 24 hours culturing, are significantly lower than that of the control group (P<0.001, N=8), which has stated that, the culturing system with the life water having been treated by different pulse intensions, for the H-MSC cells subjected to the 2% DMSO-induced injury, has shown a strong adaptability to a living environment, being able to significantly inhibit the cells from injury and apoptosis, having a certain repair effect.

5.2 Positive Induction Reagent Induced H-MSC Cells Injury Experiment.

5.2.1 Grouping and Culturing

Grouping and culturing are same as the step 3.1 in the embodiment 3

5.2.2 Measuring the Cell Mortality Number of the H-MSC Cells

Each group has three cells arranged as a parallel control, and after inoculating the cells for 24 hours, each group of cells is changed to a culture medium with a positive induction reagent containing 1/1250 primary liquid, then a death dye Ki488 with a final concentration of 1 μM is added, while monitoring the cells by a real-time dynamic imaging system, observing a variation condition of the injury and death number of the H-MSC cells induced by the positive induction reagent.

5.2.3 Measurement Results

Figure 7:
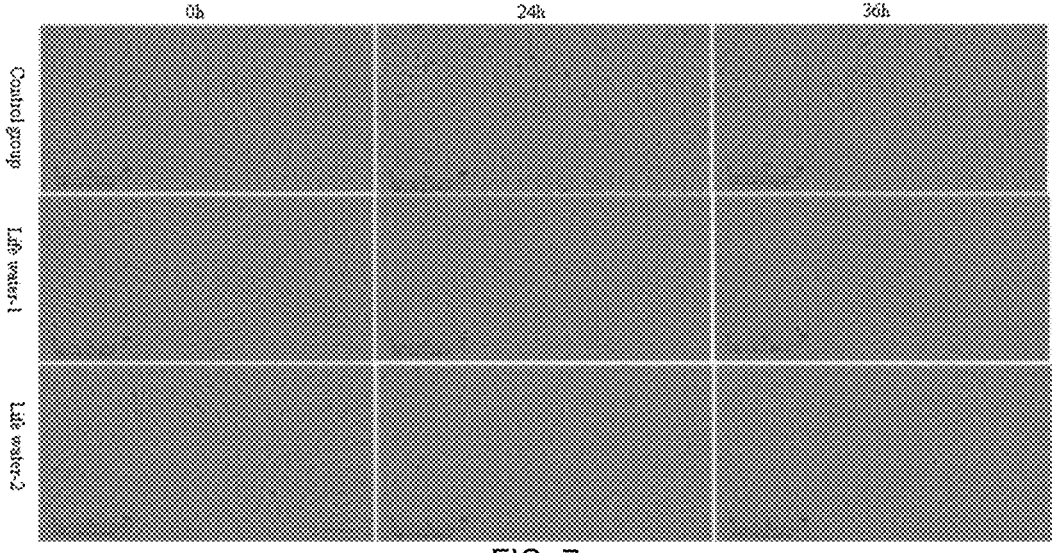
FIG. 7 illustrates a monitoring graph on a variation of a positive reagent induced injury and death of the H-MSC cells by the real-time dynamic imaging system.
Figure 8:
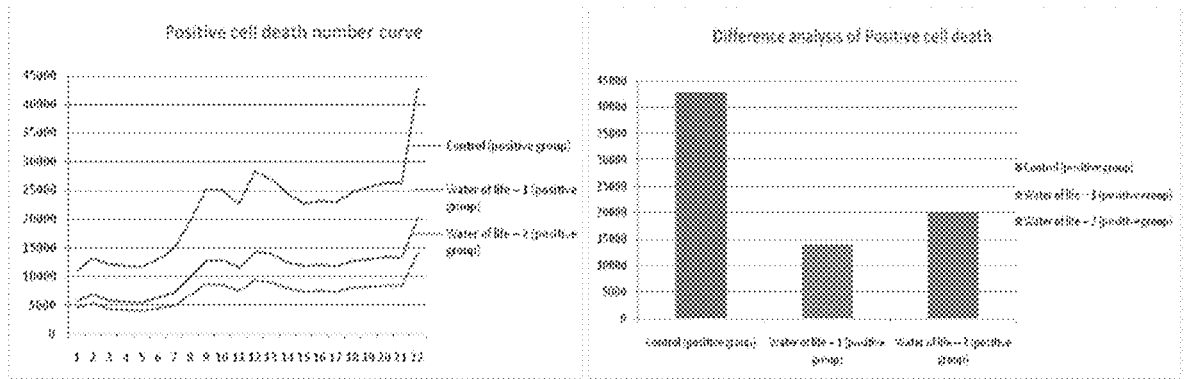

A monitoring result of the cells by the real-time dynamic imaging system is shown as FIG. 7, the H-MSC cells in the control group has a significant death after being induced by the positive induction reagent containing 1/1250 primary liquid, compared with the control group, the H-MSC cells death in the life water-1 group and the life water-2 group are significantly reduced. A result of FIG. 8 shows that, a death curve of the H-MSC cells in the life water-1 group and the life water-2 group after being induced by the positive induction reagent containing 1/1250 primary liquid are slower and lower than that of the control group; the cell death number, after 24 hours culturing, are significantly lower than that of the control group (P<0.001, N=8), which has stated that, the culturing system with the life water having been treated by different pulse intensions, for the H-MSC cells subjected to the positive induction reagent induced apoptosis, has shown an anti-infection ability and a detoxification function of the cells far surpassed that of the control group, slowing down the cell death, having a cell viability stronger than that of the control group, having a significant difference, being able to significantly inhibit cells injury and apoptosis, and having a certain repair effect.

All above, when culturing the H-MSC cells in the culturing medium prepared with the ultrapure water treated by the pulse meter, there is not only no affect on a normal proliferation of the H-MSC cells, but also being able to significantly inhibit the natural apoptosis/injury and inducted apoptosis/injury of the H-MSC cells, having an effect of repairing the stem cells.

What is claimed is:

1. A method for repairing stem cells in vitro, comprising:
   (1) resuscitating, regenerating and amplifying a plurality of stem cells;
   (2) using pulse wave treated ultrapure water to dissolve Gibco/DMEM dry powder culture medium, before reaching a constant volume of 1 L, to prepare and obtain an induction culture medium;
   (3) after inoculating the plurality of stem cells in an inoculation medium and culturing for 24 hours, replacing the inoculation medium by the induction culture medium to obtain an induction culture.

2. The method according to claim 1, wherein the plurality of stem cells comprise embryonic stem cells, umbilical cord stem cells, placenta stem cells, neural stem cells, muscle stem cells, and umbilical cord blood stem cells.

3. The method according to claim 2, wherein the plurality of stem cells are human umbilical cord mesenchymal stem cells.

4. The method according to claim 1, wherein the pulse wave treated ultrapure water is prepared by a method comprising adopting a pulse wave with a power of 28W and a frequency of 1.5M, to radiate and treat ultrapure water, the pulse wave comprises a plurality of repeated pulse sequences, the plurality of repeated pulse sequence comprises a first pulse sequence and a second pulse sequence in an interval, wherein both the first pulse sequence and the second pulse sequence comprise four pulses and four intervals, a width of the four pulses of the first pulse sequence is equal, a range of the width of the pulse is 1.3-3.5 μs, the intervals between the each of the four pulses and a subsequent pulse are equal, and a range of the interval between the pulses is 0.7-3.1 μs; a width of the four pulses of the second pulse sequence is equal, and a range of the width of the pulse is 1.1-3.9 μs, a first pulse and a third pulse have an interval between the pulses and a subsequent pulse that is equal, a range of the interval between the pulses is 1.8-4.6 μs, a second pulse and a fourth pulse have an interval between the pulses and a subsequent pulse that is equal, a range of the interval between the pulses is 0.9-2.3 μs.

5. The method according to claim 1, wherein the pulse wave treated ultrapure water is prepared by a method comprising adopting a pulse wave with a power of 35W and a frequency of 1.9M, to radiate and treat ultrapure water, the pulse wave comprises a plurality of repeated pulse sequences, the plurality of repeated pulse sequence comprises a first pulse sequence and a second pulse sequence in an interval, wherein both the first pulse sequence and the second pulse sequence comprise four pulses and four intervals, a width of the four pulses of the first pulse sequence is equal, a range of the width of the pulse is 1.3-3.5 μs, the intervals between the each of the four pulses and a subsequent pulse are equal, and a range of the interval between the pulses is 0.7-3.1 μs; a width of the four pulses of the second pulse sequence is equal, and a range of the width of the pulse is 1.1-3.9 μs, a first pulse and a third pulse have an interval between the pulses and a subsequent pulse that is equal, a range of the interval between the pulses is 1.8-4.6 μs, a second pulse and a fourth pulse have an interval between the pulses and a subsequent pulse that is equal, a range of the interval between the pulses is 0.9-2.3 μs.

* * * * *